(12) United States Patent
Withagen et al.

(10) Patent No.: US 11,331,067 B2
(45) Date of Patent: May 17, 2022

(54) DEVICE, SYSTEM AND METHOD FOR CONTROLLING A POSITION OF AN ANTI-SCATTER GRID IN AN X-RAY IMAGE ACQUISITION SYSTEM

(71) Applicant: KONINKLIJKE PHILIPS N.V., Eindhoven (NL)

(72) Inventors: Petrus Johannes Withagen, Halsteren (NL); Erik Hummel, Eindhoven (NL); Peter George Van De Haar, Eindhoven (NL); Fred Simon Berend Van Nijnatten, Eindhoven (NL); Joost Adrianus Van Rooijen, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 38 days.

(21) Appl. No.: 17/040,701

(22) PCT Filed: Mar. 25, 2019

(86) PCT No.: PCT/EP2019/057350
§ 371 (c)(1),
(2) Date: Sep. 23, 2020

(87) PCT Pub. No.: WO2019/185496
PCT Pub. Date: Oct. 3, 2019

(65) Prior Publication Data
US 2021/0007700 A1    Jan. 14, 2021

(30) Foreign Application Priority Data

Mar. 27, 2018   (EP) .................................... 18164325

(51) Int. Cl.
*A61B 6/00* (2006.01)

(52) U.S. Cl.
CPC ............ *A61B 6/547* (2013.01); *A61B 6/4291* (2013.01); *A61B 6/4441* (2013.01); *A61B 6/587* (2013.01)

(58) Field of Classification Search
CPC ....... A61B 6/547; A61B 6/587; A61B 6/4441; A61B 6/484; A61B 6/06; A61B 6/4035;
(Continued)

(56) References Cited

U.S. PATENT DOCUMENTS

| 5,469,429 A | 11/1995 | Yamazaki et al. |
| 7,581,884 B1 | 9/2009 | Barnes et al. |

(Continued)

FOREIGN PATENT DOCUMENTS

| JP | 2009183373 A | 8/2009 |
| KR | 2016086211 A | 7/2016 |
| WO | 2010133920 A1 | 11/2010 |

OTHER PUBLICATIONS

Barnes et al: "The Scanning Grid: A Novel and Effective Bucky Movement"; Radiology, vol. 135, pp. 765-767, Jun. 1980.
(Continued)

*Primary Examiner* — Don K Wong

(57) ABSTRACT

The present invention relates to a device for controlling a position of an anti-scatter grid in an X-ray image acquisition system, the device (10) comprising: a measurement unit (12); a control unit (14); and a shifting unit (16); wherein the measurement unit (12) is configured to determine an X-ray beam focus position (37) of an X-ray radiation source of the X-ray image acquisition system with respect to an X-ray detector of the X-ray image acquisition system; wherein the control unit (14) is configured to generate a shifting signal based on a displacement (18) between the X-ray beam focus position (37) and a grid focus position (35) of the anti-scatter grid; and wherein, based on the shifting signal, the shifting unit (16) is configured to shift an anti-scatter grid of the
(Continued)

X-ray image acquisition system in at least one direction to align the anti-scatter grid with the X-ray beam focus position (37), provides an improved anti-scatter grid for X-ray acquisition systems. The invention provides the use of an improved anti-scatter grid (26) for X-ray acquisition systems (20).

12 Claims, 3 Drawing Sheets

(58) Field of Classification Search
CPC ........ G61B 6/4291; G21K 1/025; G21K 1/10; G21K 1/04; G01N 2223/051; G01N 23/201; G01N 23/203
See application file for complete search history.

(56) References Cited

U.S. PATENT DOCUMENTS

| | | |
|---|---|---|
| 9,247,914 B2 | 2/2016 | Konno et al. |
| 2002/0080922 A1 | 6/2002 | Kwasnick et al. |
| 2008/0088059 A1* | 4/2008 | Tang .................. G21K 1/025 264/261 |
| 2009/0238324 A1 | 9/2009 | Oikawa et al. |
| 2014/0042333 A1 | 2/2014 | Niederlohner et al. |
| 2015/0103972 A1 | 4/2015 | Bredno et al. |
| 2016/0022230 A1 | 1/2016 | Farbizio et al. |
| 2016/0247590 A1 | 8/2016 | Young |

OTHER PUBLICATIONS

PCT/EP2019057350, ISR & WO, dated May 31, 2019, 15 Page Document.

* cited by examiner

DEVICE, SYSTEM AND METHOD FOR CONTROLLING A POSITION OF AN ANTI-SCATTER GRID IN AN X-RAY IMAGE ACQUISITION SYSTEM

CROSS-REFERENCE TO PRIOR APPLICATIONS

This application is the U.S. National Phase application under 35 U.S.C. § 371 of International Application No. PCT/EP2019/057359, filed on Mar. 25, 2019, which claims the benefit of European Patent Application No. 181643125.5, filed on Mar. 27, 2018 These applications are hereby incorporated by reference herein.

FIELD OF THE INVENTION

The present invention relates to a device, a system and a method for controlling a position of an anti-scatter grid in an X-ray image acquisition system.

BACKGROUND OF THE INVENTION

For acquiring X-ray images, an X-ray radiation source emits X-ray radiation from a focal spot that is defined by the position where an electron beam hits an anode of the X-ray radiation source. The X-ray radiation travels through an object and gratings to an X-ray detector. On the travelling path, the X-ray radiation is scattered which results in a significant source of noise in the X-ray image. Scatter can be reduced using an anti-scatter grid, which is a plate in front of the X-ray detector that has lead or a similarly high absorbing material such as tungsten strips that are positioned such that only X-ray radiation originating from the focal spot can pass through wherein other (scattered) X-ray radiation will be absorbed.

In computed tomography systems two-dimensional anti-scatter grids having a height of several cm are used which absorb a significant amount of scatter. However, in C-arm systems the anti-scatter grid only has a height of 2 to 3 mm since C-arm X-ray systems are not infinitely rigid. Depending on the orientation, speed and acceleration the exact position of the focal spot with respect to the X-ray detector may vary.

U.S. Pat. No. 5,469,429 A relates to a device which aligns the focal spot to a predetermined position in a computed tomography system. The device detects the focal spot of the X-ray radiation on the anode of the X-ray tube. Then, the device adjusts the position of the focal spot to the predetermined position by repositioning the anode or by changing the path of the electron beam.

SUMMARY OF THE INVENTION

There may be a need for a device and a method which provides the use of an improved anti-scatter grid for X-ray acquisition systems.

The object of the present invention is solved by the subject-matter of the independent claims; further embodiments are incorporated in the dependent claims. It should be noted that the following described aspects of the invention apply also for the system, the X-ray image acquisition system, the method, the computer program element, and the computer readable medium.

According to an aspect of the present invention, an X-ray image acquisition system is provided, comprising an X-ray radiation source and an X-ray detector connected to at least one C-arm as a support structure, and an anti-scatter grid arranged between an object receiving space and the X-ray detector. The system further includes a device for controlling a position of the anti-scatter grid, comprising a measurement unit, a control unit and a shifting unit. The measurement unit is configured to determine an X-ray beam focus position of the X-ray radiation source with respect to the X-ray detector. The control unit is configured to generate a shifting signal based on a displacement between the X-ray beam focus position and a grid focus position of the anti-scatter grid. The shifting unit is configured to, based on the shifting signal, shift the anti-scatter grid in at least one direction to align the anti-scatter grid with the X-ray beam focus position.

The device therefore adapts the position of the anti-scatter grid to align the grid focus position of the anti-scatter grid to the X-ray beam focus position. The device first measures the focus position of the X-ray radiation beam in the X-ray radiation source. Furthermore, the displacement between the measured X-ray beam focus position and the grid focus position of the anti-scatter grid of the X-ray image acquisition system is determined. Depending on the displacement, a shifting signal is generated which comprises the information how much the anti-scatter grid should be shifted in order to align the grid focus position to the X-ray beam focus position. The shifting unit then shifts the anti-scatter grid according to the information of the shifting signal. A displacement between the X-ray radiation source and the anti-scatter grid which may for example occur due to deformations of the structure of the X-ray image acquisition system may therefore be compensated by shifting the anti-scatter grid into a position in which the X-ray radiation may pass the anti-scatter grid. Due to the compensation of a misalignment between the X-ray beam focus position and the grid focus position thick anti-scatter grids, i.e. anti-scatter grids having a high grid ratio, may be used. The use of anti-scatter grids having a high grid ratio results in an improvement of the image quality since the contrast of the X-ray image is improved due to the reduction of scatter.

In an example, the anti-scatter grid is arranged between an object receiving space and the X-ray detector, the object receiving space being a space between the X-ray radiation source and the X-ray detector. The anti-scatter grid may for example be arranged close in front of the X-ray detector. In another example, the anti-scatter grid may be arranged on the X-ray detector.

In an example, the shifting unit is connected to an anti-scatter grid of the X-ray image acquisition system.

According to an example, the control unit is configured to determine the displacement based on an analysis of an X-ray image that is acquired by the X-ray detector.

In an example, the analysis of an X-ray image comprises a contrast analysis.

In an example, the determination of the displacement is performed based on the anti-scatter grid position with respect to the X-ray radiation source.

In an example, the control unit is configured to determine whether the X-ray image depicts a shadow of the anti-scatter grid, the shadow indicating the displacement.

According to an example, the shifting unit is configured to shift the anti-scatter grid in at least one direction that is arranged in a plane being parallel to an X-ray impact surface of the X-ray detector.

In an example, the anti-scatter grid is a 1D grid.

According to an example, the shifting unit is configured to shift the anti-scatter grid in two directions. In an example, the anti-scatter grid is a 2D grid. This further improves the scatter removal.

According to an example, the shifting unit comprises at least one control member that is configured to move the anti-scatter grid.

In an example, the control member is a motor.

According to an example, the measurement unit is configured to determine the X-ray beam focus position during an acquisition of an X-ray image with the X-ray image acquisition system. Deviations of the alignment between the X-ray beam focus position and the grid focus position may therefore be compensated during the acquisition of an X-ray image. Hence, a repeated image acquisition on the same position due to low contrast is avoided.

In an example, the measurement unit is configured to determine the actual position during a calibration procedure before the acquisition of an X-ray image with the image acquisition system.

According to an example, the X-ray radiation source and the X-ray detector are mounted to opposing sections of the C-arm as at least one support structure; and wherein the support structure is configured to rotate the two opposing attachment sections around the object receiving space.

In an example, the X-ray image acquisition is one of the group of a two-dimensional image acquisition system, a three-dimensional image acquisition system, or a mobile system.

According to an example, the control unit is configured to generate the shifting signal based on the X-ray detector's angular position, speed, and/or acceleration.

In an example, the anti-scatter grid comprises a grid ratio in the range of 8:1 to 16:1, preferably in the range of 10:1 to 16:1, most preferably in the range of 12:1 to 16:1. The grid ratio is defined to be the ratio of the grid height to the grid interspace width.

In an example, the anti-scatter grid is a high ratio grid, i.e. a "thick" anti-scatter grid.

Further examples and advantages of the X-ray image acquisition system may be derived from the above description. Thus, it is referred to the above description.

According to the present invention, also a method for controlling a position of an anti-scatter grid in a C-arm X-ray image acquisition system is provided, the method comprising the following steps: a) determining an X-ray beam focus position of an X-ray radiation source of an X-ray image acquisition system with respect to an X-ray detector of the X-ray image acquisition system using a measurement unit; b) generating a shifting signal based on a displacement between the X-ray beam focus position and the grid focus position using the control unit: c) shifting the position of the anti-scatter grid in at least one direction based on the shifting signal using a shifting unit to align the anti-scatter grid with the X-ray beam focus position in the X-ray radiation source.

Further examples and advantages of the method may be derived from the above description. Thus, it is referred to the above description.

According to the present invention, also a computer program element for controlling an apparatus according to the above description is provided, which, when being executed by a processing unit, is adapted to perform the method according to the above description.

According to the present invention, also a computer readable medium having stored the program element according to the above description is provided.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1A:
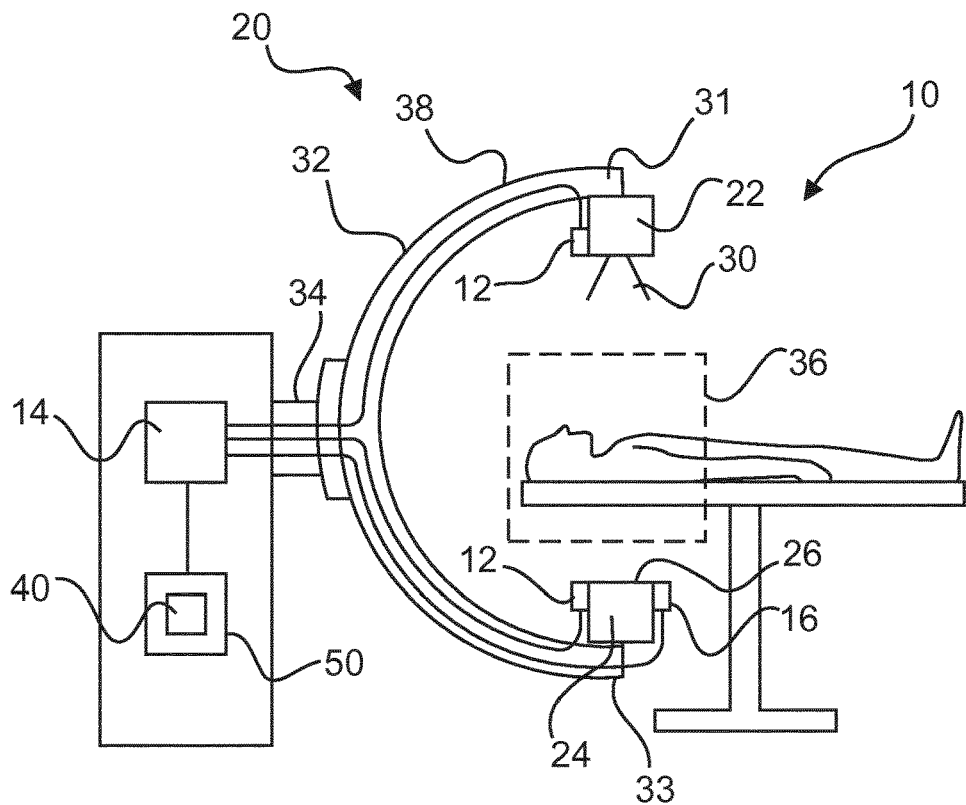
FIGS. 1a, b show schematic drawings of X-ray image acquisition systems.
Figure 1B:
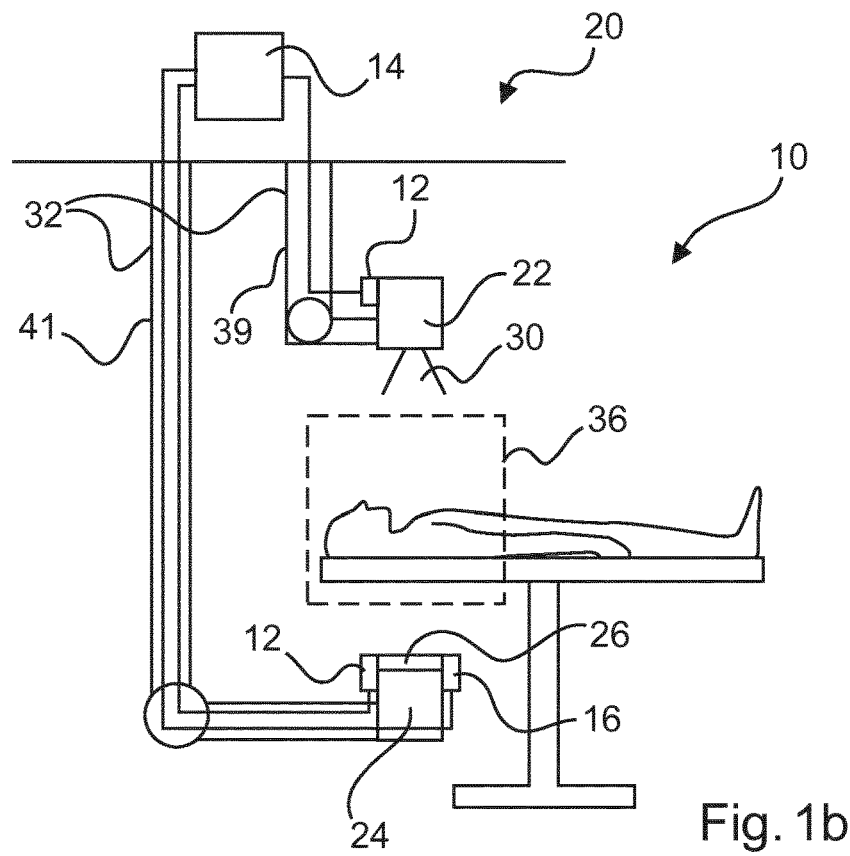

FIGS. 1a and 1b show an X-ray image acquisition system 20 comprising an X-ray radiation source 22, an X-ray detector 24, an anti-scatter grid 26, at least one support structure 32, and a device 10 for controlling a position of an anti-scatter grid in an X-ray image acquisition system. The device 10 comprises a measurement unit 12, a control unit 14, and a shifting unit 16.

In an embodiment of the invention, the X-ray image acquisition system 20 may be a two-dimensional X-ray image acquisition system.

In another embodiment of the invention, the X-ray image acquisition system 20 may be a three-dimensional X-ray image acquisition system.

In a further embodiment of the invention, the X-ray image acquisition system 20 may be a mobile X-ray image acquisition system.

The X-ray radiation source 22 emits X-ray radiation 30 from an X-ray beam focus position 37. The X-ray radiation 30 travels through an object receiving space 36, in which for example a patient to be examined may be present, and the anti-scatter grid 26 and then arrives on an X-ray impact surface 43 of the X-ray detector 24. The anti-scatter grid 26 filters scattered X-ray radiation, only letting through X-ray radiation 30 which is emitted from the grid focus position 35 of the anti-scatter grid 26.

The anti-scatter grid 26 may comprise a grid ratio in the range of 8:1 to 16:1, preferably in the range of 10:1 to 16:1, most preferably in the range of 12:1 to 16:1. The grid ratio is defined to be the ratio of the grid height to the grid interspace width. An anti-scatter grid 26 having a high grid ratio may be called a thick anti-scatter grid. The thick anti-scatter grid will highly reduce the scatter in the X-ray image which will highly improve the quality of the X-ray images due to the reduced signal-to-noise ratio.

In FIG. 1a, the at least one support structure 32 is a C-arm 38. The C-arm comprises two opposing sections 31, 33 which are arranged at opposing ends of the C-arm 38. The X-ray radiation source 22 is attached to the first opposing section 31. The X-ray detector 24 is attached to the second opposing section 33. The at least one support structure 32 may rotate the two opposing sections 31, 33 with the X-ray radiation source 22 and the X-ray detector 24, respectively, around the object receiving space 36. The rotation may be performed around an axis 34 which serves a rotational bearing for the support structure 32.

In FIG. 1b, the at least one support structure 32 comprises two robotic arms 39, 41. The X-ray radiation source 22 is attached to the first robotic arm 39. The X-ray detector 24 is attached to the second robotic arm 41. The robotic arms 39, 41 may rotate the X-ray radiation source 22 and the X-ray detector 24 around the object receiving space 36. Furthermore, the robotic arms 39, 41 are configured to arrange the X-ray radiation source 22 and the X-ray detector 24 on opposing sides of the object receiving space 36 during the image acquisition process. The X-ray radiation 30 emitted by the X-ray radiation source 22 may therefore travel through the object receiving space 36 to the X-ray detector 24.

Figure 2A:
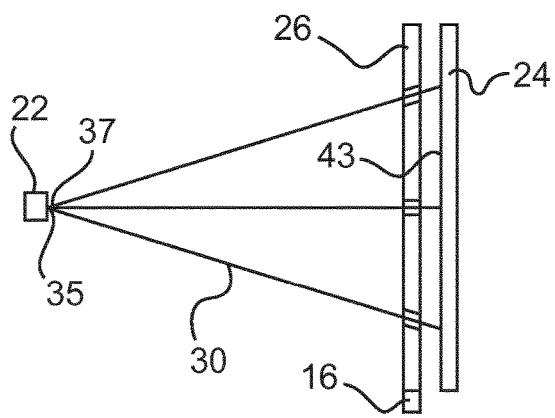
FIG. 2a-c show schematic drawings of the shift of an anti-scatter grid.

As long as the X-ray beam focus position 37 and the grid focus position 35 match, the X-ray radiation 30 passing the anti-scatter grid 26 will provide a high-quality image of an object in the object receiving space 36. This is shown in FIG. 2a.

Figure 2B:
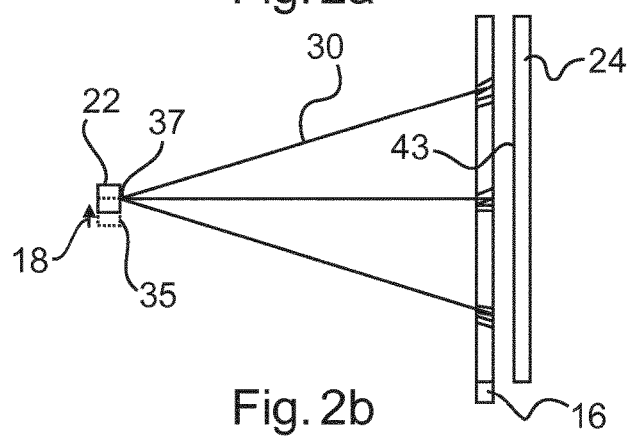

FIG. 2b shows the situation, that the X-ray beam focus position 37 deviates from the grid focus position 35 by a displacement 18. The anti-scatter grid 26 will then filter some of the X-ray radiation 30 being emitted from the X-ray beam focus position 37 such that the image quality on the X-ray detector 24 will be reduced. Such a deviation may result during the image acquisition due to deformations of the at least one support structure 32. The deformations may for example occur due to acceleration and/or gravitational forces during the rotation of the at least one support structure 32 around the object receiving space 36.

Figure 2C:
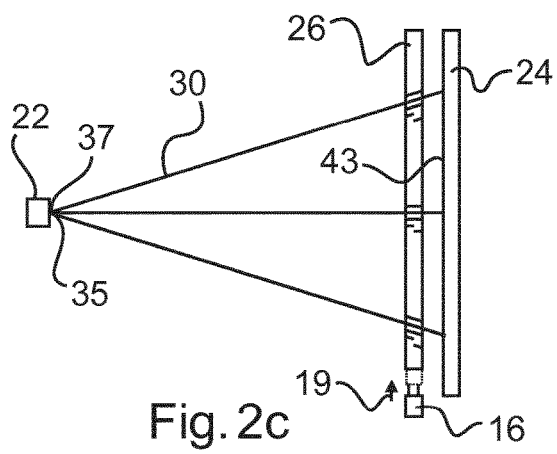

In order to align the grid focus position 35 of the anti-scatter grid 26 to the X-ray beam focus position 37, the shifting unit 16 may shift the anti-scatter grid 26 by a distance 19, according to FIG. 2c, such that the X-ray radiation 30 that is emitted from the X-ray beam focus position 37 may pass the anti-scatter grid 26. The shift of the anti-scatter grid 26 may be performed parallel to the X-ray impact surface 43.

Figure 3:
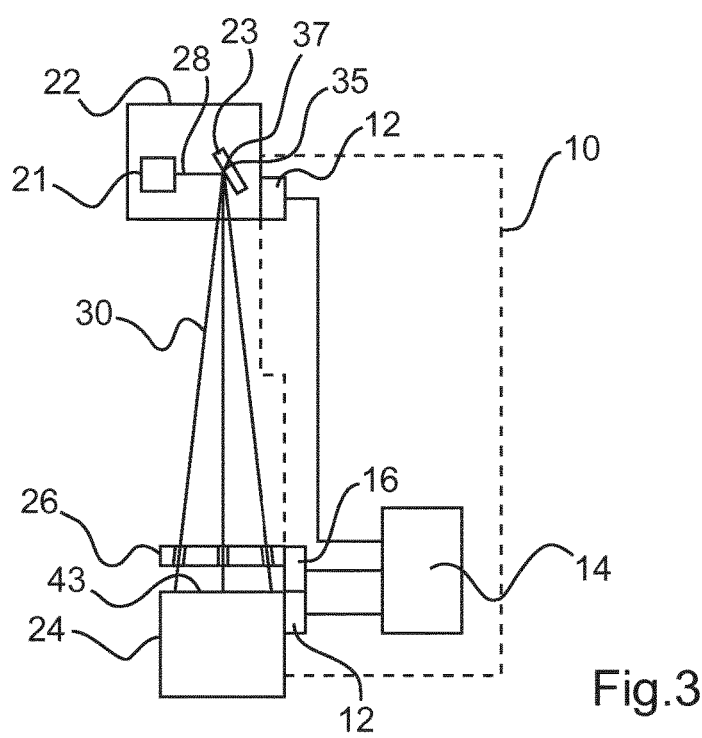
FIG. 3 shows a schematic drawing of a device for controlling a position of an anti-scatter grid in an X-ray image acquisition system.

FIG. 3 shows device 10 in more detail. The measurement unit 12 may comprise two elements which may be arranged at the X-ray radiation source 22 and the X-ray detector 24. The measurement unit 12 is configured to determine the X-ray beam focus position 37 in the X-ray radiation source 22 with respect to the X-ray detector 24. The X-ray beam focus position 37 is determined by the position in the X-ray radiation source 22 on which an electron beam 28 being emitted from a cathode 21 arrives at the anode 23.

The measurement unit 12 determines the position of the X-ray detector 24 and compares it to the position of the X-ray beam focus position 37 in order to determine a displacement between the X-ray beam focus position 37 and the X-ray detector 24. The measurement unit 12 may provide that determination during an image acquisition process.

For determining a displacement between the X-ray beam focus position 37 to the X-ray detector 24, an initial alignment between the X-ray beam focus position 37 in the X-ray radiation source 22 and the grid focus position 35 of the anti-scatter grid 26 which may be arranged close to or on the X-ray detector 24, respectively, may be provided. The measurement unit 12 may determine deviations between an initial spatial alignment of the X-ray radiation source 22 and the X-ray detector 24 during the image acquisition, i.e. during the rotation of the X-ray radiation source 22 and the X-ray detector 24 around the object receiving space 36. Then, the measurement unit 12 may determine any displacement to the initial alignment during the image acquisition.

Additionally, in an example, a displacement 18 between the X-ray beam focus position 37 and the grid focus position 35 may be determined during the image acquisition by analyzing the acquired X-ray images of the X-ray detector 24. A reduction of the quality of the X-ray images will indicate a misalignment between the X-ray beam focus position 37 and the grid focus position 35. The reduction of the quality may result from a reduction of the contrast of the X-ray image and/or from the presence of a shadow of the anti-scatter grid 26 in the X-ray image. This may improve the determination of the displacement between the X-ray beam focus position 37 and the grid focus position 35.

The control unit 14 analyzes the measured displacement 18 between the X-ray position 37 and the grid focus position 35. Based on the displacement 18 the control unit 14 generates a shifting signal. The shifting signal comprises information about the distance 19 that the anti-scatter grid 26 has to be shifted in order to align the grid focus position 35 to the X-ray beam focus position 37.

The control unit 14 may also base the shifting signal on the X-ray detector's 24 angular position, speed, and/or acceleration. The angular position, the speed, and the acceleration may be acquired by sensors on the at least one support structure 32.

The shifting unit 16 may be attached to the anti-scatter grid 26. Furthermore, the shifting unit 16 may comprise at least one control member that may be motor. The control member is configured to reposition the anti-scatter grid 26 in one dimension, i.e. along one direction.

The shifting unit 16 receives the shifting signal from the control unit 14 and shifts the anti-scatter grid 26 by the distance 19. This shifts the grid focus position 35 towards the X-ray beam focus position 37. The result is a realignment of the X-ray beam focus position 37 to the grid focus position 35 of the anti-scatter grid 26.

Figure 4A:
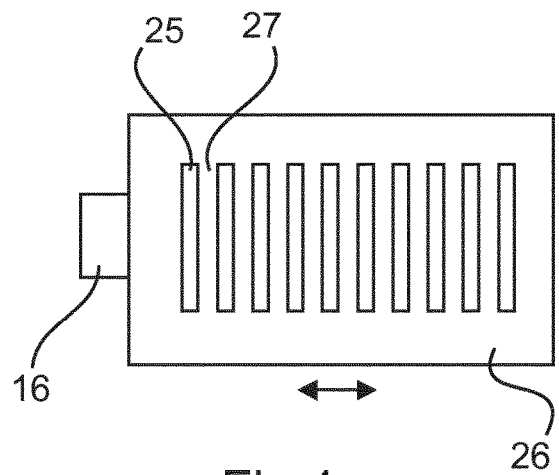
FIG. 4 shows a schematic drawing of a two-dimensional anti-scatter grid.
Figure 4B:
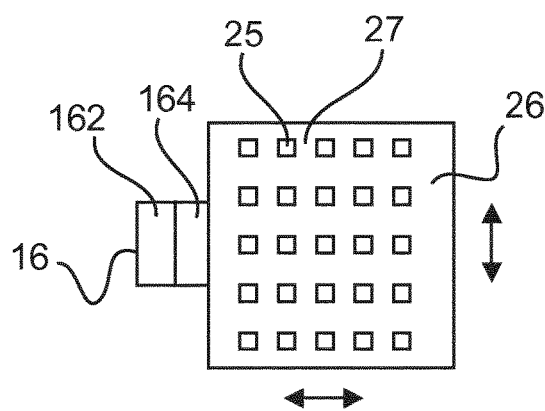

FIGS. 4a and 4b show different types of anti-scatter grids 26. FIG. 4a shows a one-dimensional anti-scatter grid 26. This one-dimensional anti-scatter grid 26 comprises a single row of X-ray radiation transparent sections 25 which are separated by X-ray radiation absorbing sections 27. The X-ray radiation transparent sections 25 are arranged such that they are aligned to the grid focus position 35. The one-dimensional anti-scatter grid 26 may reduce the scatter in one dimension.

The shifting unit 16 being attached to the anti-scatter grid 26 may reposition the anti-scatter grid 26 in the direction indicated by the arrow.

FIG. 4b shows a two-dimensional anti-scatter grid 26. The two-dimensional anti-scatter grid 26 has several rows of X-ray radiation transparent sections 25 which are separated by X-ray radiation absorbing sections 27. Also, the rows of the X-ray radiation transparent sections 25 are separated by X-ray radiation absorbing sections 27. That two-dimensional anti-scatter grid 26 may reduce the scatter in two dimensions.

The shifting unit 16 comprises a first shifting component 162 and a second shifting component 164. The first and the second shifting components 162, 164 may be control members.

The first shifting component 162 may shift the anti-scatter grid 26 in a first dimension wherein the second shifting component 164 may shift the anti-scatter grid 26 in a second dimension. The first and the second dimension may be orthogonal with respect to each other indicated by the arrows. However, the first and the second dimension may also be non-orthogonal while being non-parallel.

Figure 5:
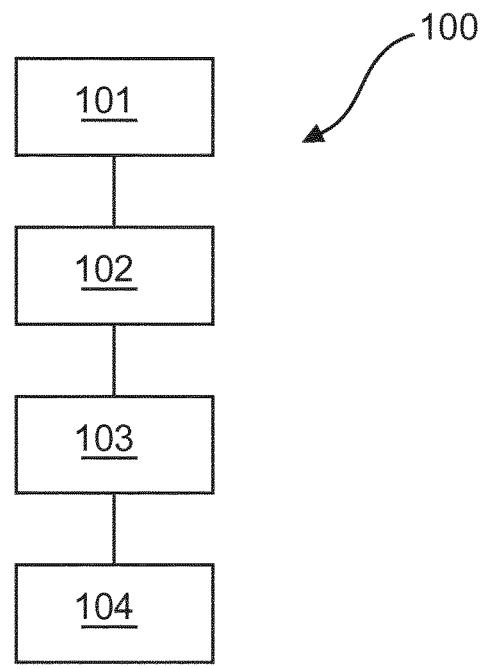
FIG. 5 shows a schematic flow chart of the method.

FIG. 5 shows a flowchart for the method 100 for controlling the position of the anti-scatter grid in an X-ray image acquisition system.

In step a), and X-ray beam focus position of an X-ray radiation source of an X-ray image acquisition system is determined 101 with respect to an X-ray detector of the X-ray image acquisition system using a measurement unit.

The position of the X-ray detector and the X-ray radiation source may be determined in order to determine changes in the alignment of the anti-scatter grid being arranged close to or on the X-ray detector, respectively, to the X-ray beam focus position. This means, that in step a), the displacement between the grid focus position and the X-ray beam focus position may be determined.

In an example, in addition, acquired X-ray images may be analyzed 102 to determine a reduction of the image quality, wherein the reduction may result from a reduced contrast and/or a shadow of an anti-scatter grid in the X-ray image due to a change of alignment. This may improve the determination of the displacement between the grid focus position and the X-ray beam focus position.

In step b), a shifting signal is generated 103 from the displacement between the X-ray beam focus position and the grid focus position. The generation 102 may be performed by a control unit. The shifting signal comprises the information how much the anti-scatter grid must be repositioned in order to align the grid focus position of the anti-scatter grid to the X-ray beam focus position.

In step c), the position of the anti-scatter grid may be shifted 104 in at least one direction based on the shifting signal. This shifting may be performed by a shifting unit. This will align the grid focus position of the anti-scatter grid to the X-ray beam focus position in the X-ray radiation source.

In another exemplary embodiment of the present invention, a computer program or a computer program element 40 being shown in FIG. 1 is provided that is characterized by being adapted to execute the method steps of the method according to one of the preceding embodiments, on an appropriate system.

The computer program element 40 might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium 50 according to FIG. 1, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray image acquisition system, comprising:
an X-ray radiation source and an X-ray detector connected to at least one C-arm as a support structure;
an anti-scatter grid arranged between an object receiving space and the X-ray detector; and
a device for controlling a position of the anti-scatter grid comprising:
a measurement unit;
a control unit; and
a shifting unit;
wherein the measurement unit is configured to determine an X-ray beam focus position of the X-ray radiation source with respect to the X-ray detector;
wherein the control unit is configured to generate a shifting signal based on a displacement between the X-ray beam focus position and a grid focus position of the anti-scatter grid; and
wherein, based on the shifting signal, the shifting unit is configured to shift the anti-scatter grid in at least one direction to align the anti-scatter grid with the X-ray beam focus position.

2. The X-ray image acquisition system according to claim 1, wherein the anti-scatter grid comprises a grid ratio in a range of 8:1 to 16:1.

3. The X-ray image acquisition system according to claim 1, wherein the control unit is configured to determine the displacement based on an analysis of an X-ray image that is acquired by the X-ray detector.

4. The X-ray image acquisition system according to claim 1, wherein the shifting unit is configured to shift the anti-scatter grid in at least one direction that is arranged in a plane being parallel to an X-ray impact surface of the X-ray detector.

5. The X-ray image acquisition system according to claim 1, wherein the shifting unit is configured to shift the anti-scatter grid in two directions.

6. The X-ray image acquisition system according to claim 1, wherein the shifting unit comprises at least one control member that is configured to move the anti-scatter grid.

7. The X-ray image acquisition system according to claim 1, wherein the measurement unit is configured to determine the X-ray beam focus position during an acquisition of an X-ray image with the X-ray image acquisition system.

8. The X-ray image acquisition system according to claim 1 wherein the X-ray radiation source and the X-ray detector are mounted to opposing sections of the at least one C-arm; and wherein the at least one C-arm is configured to rotate the opposing sections, around the object receiving space.

9. The X-ray image acquisition system according to claim 1, wherein the control unit is configured to generate the shifting signal based on the X-ray detector's angular position, speed, and/or acceleration.

10. A method for controlling a position of an anti-scatter grid in a C-arm X-ray image acquisition system, the method comprising:
a) determining an X-ray beam focus position of an X-ray radiation source of the C-arm X-ray image acquisition system with respect to an X-ray detector of the C-arm X-ray image acquisition system using a measurement unit;
b) generating a shifting signal based on a displacement between the X-ray beam focus position and a grid focus position using a control unit; and
c) shifting the position of the anti-scatter grid in at least one direction based on the shifting signal using a shifting unit to align the anti-scatter grid with the X-ray beam focus position in the X-ray radiation source.

11. A computer program element for controlling an X-ray image acquisition system, comprising:
an X-ray radiation source and an X-ray detector connected to at least one C-arm as a support structure;
an anti-scatter grid arranged between an object receiving space and the X-ray detector; and
a device for controlling a position of the anti-scatter grid comprising:
a measurement unit;
a control unit; and
a shifting unit;
wherein the measurement unit is configured to determine an X-ray beam focus position of the X-ray radiation source with respect to the X-ray detector;
wherein the control unit is configured to generate a shifting signal based on a displacement between the X-ray beam focus position and a grid focus position of the anti-scatter grid; and
wherein, based on the shifting signal, the shifting unit is configured to shift the anti-scatter grid in at least one direction to align the anti-scatter grid with the X-ray beam focus position, which, when being executed by a processing unit, is adapted to perform the method of claim 10.

12. A non-transitory computer-readable medium having stored the computer program element of claim 11.

* * * * *